United States Patent
Fujikura et al.

(10) Patent No.: US 7,465,712 B2
(45) Date of Patent: Dec. 16, 2008

(54) GLUCOPYRANOSYLOXY BENZYLBENZENE DERIVATIVES, MEDICINAL COMPOSITIONS CONTAINING THE SAME AND INTERMEDIATES FOR THE PREPARATION OF THE DERIVATIVES

(75) Inventors: Hideki Fujikura, Nagano (JP); Nobuhiko Fushimi, Nagano (JP); Toshihiro Nishimura, Nagano (JP); Kazuya Tatani, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 1282 days.

(21) Appl. No.: 10/221,843

(22) PCT Filed: Mar. 15, 2001

(86) PCT No.: PCT/JP01/02041
§ 371 (c)(1),
(2), (4) Date: Dec. 30, 2002

(87) PCT Pub. No.: WO01/68660
PCT Pub. Date: Sep. 20, 2001

(65) Prior Publication Data
US 2004/0053855 A1    Mar. 18, 2004

(30) Foreign Application Priority Data
Mar. 17, 2000 (JP) .............................. 2000-077304

(51) Int. Cl.
A01N 43/04 (2006.01)
A61K 31/70 (2006.01)
(52) U.S. Cl. .............................. 514/27; 514/23; 514/25
(58) Field of Classification Search .................. 514/25, 514/35; 536/4.1, 18.1
See application file for complete search history.

(56) References Cited

U.S. PATENT DOCUMENTS

| 4,598,068 A | 7/1986 | Samreth et al. |
| 5,232,946 A | 8/1993 | Hurnaus et al. |
| 6,683,056 B2 * | 1/2004 | Washburn et al. ............. 514/25 |
| 2002/0111315 A1 | 8/2002 | Washburn et al. |

FOREIGN PATENT DOCUMENTS

| EP | 1 213 296 A1 | 6/2002 |
| WO | WO 01/16147 A1 | 3/2001 |
| WO | WO 01/74834 A1 | 10/2001 |

OTHER PUBLICATIONS

Akira Oku, et al.; Antidiabetic effect of T-1095, an inhibitor of Na$^+$-glucose cotransporter, in neonatally streptozotocin-treated rats; European Journal of Pharmacology 39 (2000) pp. 183-192.

* cited by examiner

Primary Examiner—Shaojia Anna Jiang
Assistant Examiner—Traviss C McIntosh, III
(74) Attorney, Agent, or Firm—Sughrue Mion, PLLC

(57) ABSTRACT

The present invention relates to glucopyranosyloxybenzylbenzene derivatives represented by the general formula:

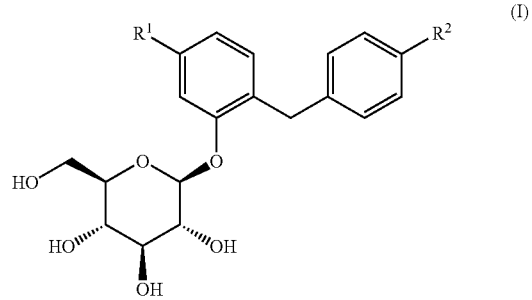

wherein $R^1$ represents a hydrogen atom or a hydroxy(lower alkyl) group; and $R^2$ represents a lower alkyl group, a lower alkoxy group, a lower alkylthio group, a hydroxy(lower alkyl) group, a hydroxy(lower alkoxy) group, a hydroxy(lower alkylthio) group etc., and salts thereof, which have an excellent inhibitory activity in human SGLT2 and are useful as agents for the prevention or treatment of diabetes, obesity etc., and intermediates thereof.

6 Claims, No Drawings

GLUCOPYRANOSYLOXY BENZYLBENZENE DERIVATIVES, MEDICINAL COMPOSITIONS CONTAINING THE SAME AND INTERMEDIATES FOR THE PREPARATION OF THE DERIVATIVES

TECHNICAL FIELD

The present invention relates to glucopyranosyloxybenzylbenzene derivatives and pharmaceutically acceptable salts thereof which are useful as medicaments, pharmaceutical compositions comprising the same and intermediates thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and agents for reducing insulin resistance have been employed as antidiabetic agents. However, biguanides and sulfonylureas show occasionally adverse effects such as lactic acidosis and hypoglysemia, respectively. In a case of using agents for reducing insulin resistance, adverse effects such as edema occasionally are observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510-1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397-404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents, which have a potent inhibitory activity in human SGLT2 and have a new mechanism, has been desired. Furthermore, since such agents promote the excretion of excess glucose though the urine and consequently the glucose accumulation in the body is decreased, they are also expected to have a preventing effect on obesity.

DISCLOSURE OF THE INVENTION

The present inventors have studied earnestly to find compounds having an inhibitory activity in human SGLT2. As a result, it was found that glucopyranosyloxybenzylbenzene derivatives represented by the following general formula (I) show an excellent inhibitory activity in human SGLT2 as mentioned below, thereby forming the basis of the present invention.

The present invention is to provide the following glucopyranosyloxybenzylbenzene derivatives and pharmaceutically acceptable salts thereof, which show an inhibitory activity in human SGLT2 in vivo and exert a hypoglycemic effect by excreting excess glucose in the urine through preventing the reabsorption of such glucose at the kidney, pharmaceutical compositions comprising the same and intermediates thereof.

This is, the present invention relates to a glucopyranosyloxybenzylbenzene derivative represented by the general formula:

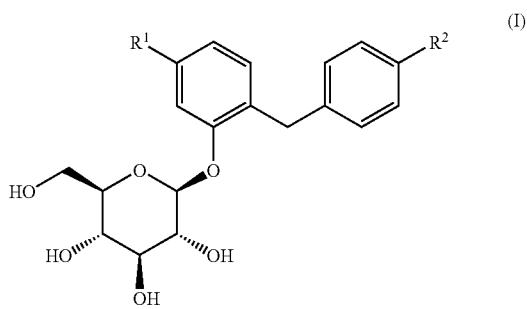

(I)

wherein $R^1$ represents a hydrogen atom or a hydroxy(lower alkyl) group; and $R^2$ represents a lower alkyl group, a lower alkoxy group, a lower alkylthio group, a hydroxy(lower alkyl) group, a hydroxy(lower alkoxy) group, a hydroxy(lower alkylthio) group, a lower alkoxy-substituted (lower alkyl) group, a lower alkoxy-substituted (lower alkoxy) group or a lower alkoxy-substituted (lower alkylthio) group, or a pharmaceutically acceptable salt thereof.

The present invention relates to a pharmaceutical composition comprising as the active ingredient a glucopyranosyloxybenzylbenzene derivative represented by the above general formula (I) or a pharmaceutically acceptable salt thereof.

The present invention relates to a method for the prevention or treatment of a disease associated with hyperglycemia, which comprises administering a glucopyranosyloxybenzylbenzene derivative represented by the above general formula (I) or a pharmaceutically acceptable salt thereof.

The present invention relates to a use of a glucopyranosyloxybenzylbenzene derivative represented by the above general formula (I) or a pharmaceutically acceptable salt thereof for the manufacture of a pharmaceutical composition for the prevention or treatment of a disease associated with hyperglycemia.

The present invention also relates to a benzylphenol derivative represented by the general formula:

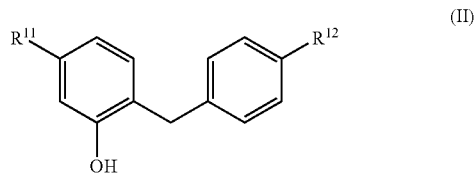

(II)

wherein $R^{11}$ represents a hydrogen atom or a protected hydroxy(lower alkyl) group; and $R^{12}$ represents a lower alkyl group, a lower alkoxy group, a lower alkylthio group, a protected hydroxy(lower alkyl) group, a protected hydroxy (lower alkoxy) group, a protected hydroxy(lower alkylthio) group, a lower alkoxy-substituted (lower alkyl) group, a lower alkoxy-substituted (lower alkoxy) group or a lower alkoxy-substituted (lower alkylthio) group; with the proviso that $R^{12}$ is not a methyl group, an ethyl group, an isopropyl group, a tert-butyl group or a methoxy group when $R^{11}$ is a hydrogen atom, or a salt thereof.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "hydroxy (lower alkyl) group" means a straight-chained or branched hydroxyalkyl group having 1 to 6 carbon atoms such as a hydroxymethyl group, a 2-hydroxyethyl group, a 1-hydroxyethyl group, a 3-hydroxypropyl group, a 2-hydroxypropyl group, a 1-hydroxypropyl group, a 2-hydroxy-1-methylethyl group, a 4-hydroxybutyl group, a 3-hydroxybutyl group, a 2-hydroxybutyl group, a 1-hydroxybutyl group, a 5-hydroxypentyl group, a 4-hydroxypentyl group, a 3-hydroxypentyl group, a 2-hydroxypentyl group, a 1-hydroxypentyl group, a 6-hydroxyhexyl group, a 5-hydroxyhexyl group, a 4-hydroxyhexyl group, a 3-hydroxyhexyl group, a 2-hydroxyhexyl group, a 1-hydroxyhexyl group or the like; the term "hydroxy (lower alkyloxy) group" means a straight-chained or branched hydroxyalkoxy group having 1 to 6 carbon atoms such as a 2-hydroxyethoxy group, a 3-hydroxypropoxy group, a 2-hydroxypropoxy group, a 2-hydroxy-1-methylethoxy group, a 4-hydroxybutoxy group, a 3-hydroxybutoxy group, a 2-hydroxybutoxy group, a 5-hydroxypentyloxy group, a 4-hydroxypentyloxy group, a 3-hydroxypentyloxy group, a 2-hydroxypentyloxy group, a 6-hydroxyhexyloxy group, a 5-hydroxyhexyloxy group, a 4-hydroxyhexyloxy group, a 3-hydroxyhexyloxy group, a 2-hydroxyhexyloxy group or the like; and the term "hydroxy (lower alkylthio) group" means a straight-chained or branched hydroxyalkylthio group having 1 to 6 carbon atoms such as a hydroxymethylthio group, a 2-hydroxyethylthio group, a 1-hydroxyethylthio group, a 3-hydroxypropylthio group, a 2-hydroxypropylthio group, a 1-hydroxypropylthio group, a 2-hydroxy-1-methylethylthio group, a 4-hydroxybutylthio group, a 3-hydroxybutylthio group, a 2-hydroxybutylthio group, a 1-hydroxybutylthio group, a 5-hydroxypentylthio group, a 4-hydroxypentylthio group, a 3-hydroxypentylthio group, a 2-hydroxypentylthio group, a 1-hydroxypentylthio group, a 6-hydroxyhexylthio group, a 5-hydroxyhexylthio group, a 4-hydroxyhexylthio group, a 3-hydroxyhexylthio group, a 2-hydroxyhexylthio group, a 1-hydroxyhexylthio group or the like. The term "lower alkoxy-substituted (lower alkyl) group means the above hydroxy(lower alkyl) group O-alkylated by the above lower alkyl group; the term "lower alkoxy-substituted (lower alkoxy) group means the above hydroxy(lower alkyloxy) group O-alkylated by the above lower alkyl group; and the term "lower alkoxy-substituted (lower alkylthio) group means the above hydroxy(lower alkylthio) group O-alkylated by the above lower alkyl group.

The term "hydroxy-protective group" means a hydroxy-protective group used in general organic reactions, such as a benzyl group, a methoxymethyl group, an acetyl group or the like.

In the substituent $R^1$, a hydrogen atom and a hydroxyalkyl group having 1 to 3 carbon atoms are preferable. In the substituent $R^2$, a lower alkyl group, a lower alkoxy group and a hydroxy(lower alkyl) group are preferable, and an alkyl group having 1 to 4 carbon atoms, an alkoxy group having 1 to 3 carbon atoms and a hydroxyalkyl group having 1 to 3 carbon atoms are more preferable.

For example, the compounds represented by the above general formula (I) of the present invention can be prepared using a benzylphenol derivative represented by the general formula (II) of the present invention according to the following procedure:

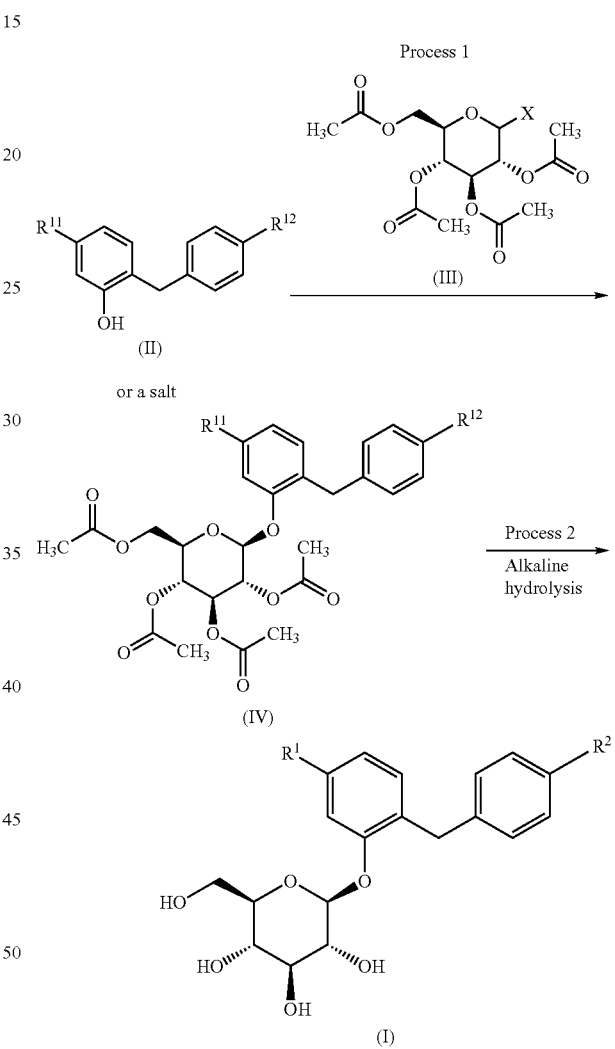

wherein $R^{11}$ represents a hydrogen atom or a protected hydroxy(lower alkyl) group; $R^{12}$ represented a lower alkyl group, a lower alkoxy group, a lower alkylthio group, a protected hydroxy(lower alkyl) group, a protected hydroxy (lower alkoxy) group, a protected hydroxy(lower alkylthio) group, an lower alkoxy-substituted (lower alkyl) group, a lower alkoxy-substituted (lower alkoxy) group or a lower alkoxy-substituted (lower alkylthio) group; X represents a leaving group such as a trichloroacetoimidoyloxy group, an acetoxy group, a bromine atom or a fluorine atom; and $R^1$ and $R^2$ have the same meanings as defined above.

Process 1

A glucoside represented by the above general formula (IV) can be prepared by subjecting a benzylphenol derivative represented by the above general formula (II) or a salt thereof to glucosidation using a glycosyl-donor represented by the above general formula (III) such as 2,3,4,6-tetra-O-acetyl-1-O-trichloroacetoimidoyl-α-D-glucopyranose, 1,2,3,4,6-penta-O-acetyl-β-D-glucopyranose, 2,3,4,6-tetra-O-acetyl-α-D-glucopyranosyl bromide and 2,3,4,6-tetra-O-acetyl-β-D-glucopyranosyl fluoride in the presence of an activating reagent such as boron trifluoride diethyl ether complex, silver trifluoromethanesulfonate, tin(IV) chloride or trimethyl-silyl trifluoromethanesulfonate in an inert solvent. As the solvent used, dichloromethane, toluene, acetonitrile, nitromethane, ethylacetate, diethylether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Process 2

A compound (I) of the present invention can be prepared by subjecting a glucoside represented by the above general formula (IV) to alkaline hydrolysis to remove the hydroxy-protective groups. As the solvent used, water, methanol, ethanol, tetrahydrofuran, a mixed solvent thereof and the like can be illustrated, and as alkaline materials, sodium hydroxide, sodium methoxide, sodium ethoxide or the like can be used. The treatment temperature is usually from 0° C. to reflux temperature, and the treatment time is usually from 30 minutes to 6 hours, varying based on a used starting material, solvent and treatment temperature. Such treatment can be carried out by suitably changing or adding an other procedure in the usual way depending on a used hydroxy-protective group.

For example, the compounds represented by the above general formula (II) of the present invention and salts thereof which are used as starting materials in the aforementioned production process can be prepared according to the following procedure:

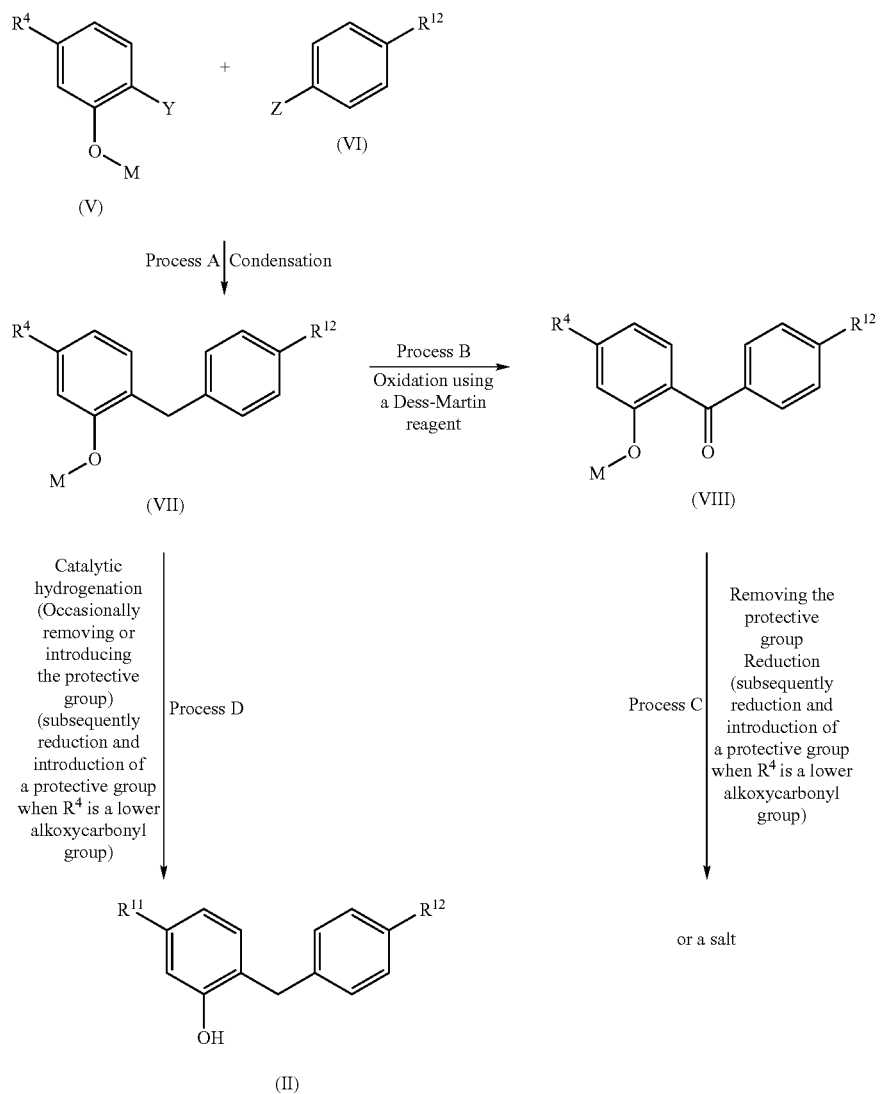

wherein M represents a hydrogen atom or a hydroxy-protective group; $R^4$ represents a hydrogen atom, a protected hydroxy(lower alkyl) group or a lower alkoxycarbonyl group; one of Y and Z is MgBr, MgCl, MgI or a lithium atom, while the other is a formyl group; and $R^{11}$ and $R^{12}$ have the same meanings as defined above.

Process A

A compound represented by the above general formula (VII) can be prepared by condensing a benzaldehyde derivative represented by the above general formula (V) with a Grignard reagent or a lithium reagent represented by the above general formula (VI), or by condensing a Grignard reagent or a lithium reagent represented by the above general formula (V) with a benzaldehyde derivative represented by the above general formula (VI) in an inert solvent. As the solvent used, tetrahydrofuran, diethyl ether, a mixed solvent thereof and the like can be illustrated. The reaction temperature is usually from −78° C. to reflux temperature, and the reaction time is usually from 10 minutes to 1 day, varying based on a used starting material, solvent and reaction temperature.

Process B

A compound represented by the above general formula (VIII) can be prepared by subjecting a compound represented by the above general formula (VII) to oxidation using a Dess-Martin reagent in an inert solvent. As the solvent used, dichloromethane, chloroform, acetonitrile, a mixed solvent thereof and the like can be illustrated. The reaction temperature is usually from 0° C. to reflux temperature, and the reaction time is usually from 1 hour to 1 day, varying based on a used starting material, solvent and reaction temperature.

Process C

A compound represented by the above general formula (II) can be prepared by removing the protective group M of a compound represented by the above general formula (VIII), (1) condensing the resulting compound with methyl chloroformate in the presence of a base such as triethylamine, diisopropylethylamine or N,N-dimethylaminopyridine in an inert solvent, and (2) subjecting the resulting carbonate derivative to reduction using a reducing agent such as sodium borohydride. As the solvent used in the reaction (1), tetrahydrofuran, dichloromethane, acetonitrile, ethyl acetate, diethyl ether, a mixed solvent thereof and the like can be illustrated. The reaction temperature is usually from 0° C. to reflux temperature, and the reaction time is usually from 30 minutes to 1 day, varying based on a used starting material, solvent and reaction temperature. As the solvent used in the reaction (2), a mixed solvent with tetrahydrofuran and water, and the like can be illustrated. The reaction temperature is usually from 0° C. to reflux temperature, and the reaction time is usually from 1 hour to 1 day, varying based on a used starting material, solvent and reaction temperature. In case that $R^4$ is a lower alkoxycarbonyl group, the compounds represented by the above general formula (II) of the present invention can be derived by subjecting the group to reduction into a hydroxymethyl group using a reducing agent such as lithium aluminum hydride in an inert solvent and protecting the hydroxy group in the usual way. As the solvent used in the reduction, diethyl ether, tetrahydrofuran, a mixed solvent thereof and the like can be illustrated. The reaction temperature is usually from 0° C. to reflux temperature, and the reaction time is usually from 10 minutes to 1 day, varying based on a used starting material, solvent and reaction temperature. The compound represented by the above general formula (II) of the present invention can be converted into a salt thereof such as a sodium salt or a potassium salt in the usual way.

Process D

A compound represented by the above general formula (II) of the present invention can be prepared by subjecting a compound represented by the above general formula (VII) to catalytic hydrogenation using a palladium catalyst such as palladium-carbon powder in the presence or absence of an acid such as hydrochloric acid in an inert solvent, and removing or introducing a protective group in the usual way as occasion demands. As the solvent used in the catalytic hydrogenation, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. In case that $R^4$ is a lower alkoxycarbonyl group, the compounds represented by the above general formula (II) of the present invention can be derived by subjecting the group to reduction into a hydroxymethyl group using a reducing agent such as lithium aluminum hydride in an inert solvent and protecting the hydroxy group in the usual way. As the solvent used in the reduction, diethyl ether, tetrahydrofuran, a mixed solvent thereof and the like can be illustrated. The reaction temperature is usually from 0° C. to reflux temperature, and the reaction time is usually from 10 minutes to 1 day, varying based on a used starting material, solvent and reaction temperature. The compound represented by the above general formula (II) of the present invention can be converted into a salt thereof such as a sodium salt or a potassium salt in the usual way.

The compounds of the present invention obtained by the above production process can be isolated and purified by conventional separation means such as fractional recrystallization, purification using chromatography, solvent extraction and solid phase extraction.

The glucopyranosyloxybenzylbenzene derivatives represented by the above general formula (I) of the present invention can be converted into their pharmaceutically acceptable salts in the usual way. Examples of such salts include inorganic base salts such as a sodium salt or a potassium salt.

The compounds represented by the above general formula (I) of the present invention include their hydrates and their solvates with pharmaceutically acceptable solvents such as ethanol.

The compounds represented by the above general formula (I) of the present invention and pharmaceutically acceptable salts thereof have an excellent inhibitory activity in human SGLT2 and are extremely useful as agents for the prevention or treatment of diabetes, diabetic complications, obesity or the like. For example, in the following assay for inhibitory effect on human SGLT2 activity, the compounds of the present invention exerted a potent inhibitory activity in human SGLT2.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional manner.

When the pharmaceutical compositions of the present invention are employed in the practical treatment, the dosage of a compound represented by the above general formula (I) or a pharmaceutically acceptable salt thereof of the present invention as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably.

BEST MODE FOR CARRYING OUT THE INVENTION

The present invention is further illustrated in more detail by way of the following Reference Examples, Examples and Test Examples. However, the present invention is not limited thereto.

REFERENCE EXAMPLE 1

4-(3-Benzyloxypropyl)bromobenzene

A suspension of sodium hydride (60%, 0.97 g), 3-(4-bromophenyl)-1-propanol (1.0 g) and benzyl bromide (0.69 mL) in benzene (24 mL) was stirred for 7 hours under reflux. After cooling to ambient temperature, a saturated aqueous ammonium chloride solution (50 mL) was added to the reaction mixture, and the mixture was extracted with ethyl acetate (100 mL). The organic layer was washed with water (40 mL) and brine (40 mL), and dried over anhydrous sodium sulfate. The solvent was removed under reduced pressure, and the residue was purified by column chromatography on silica gel (eluent: hexane/ethyl acetate=20/1) to give 4-(3-benzyloxypropyl)bromobenzene (1.4 g).
$^1$H-NMR (CDCl$_3$) δ ppm:
1.85-2.00 (2H, m), 2.60-2.75 (2H, m), 3.47 (2H, t, J=6.2 Hz), 4.50 (2H, s), 7.00-7.10 (2H, m), 7.20-7.45 (7H, m)

REFERENCE EXAMPLE 2

Methyl 4-(4-ethylbenzyl)-3-hydroxybenzoate

To a solution of 1-bromo-4-ethylbenzene (0.41 mL) in tetrahydrofuran (15 mL) was added 1.45 mol/L tert-butyllithium n-pentane solution (2.3 mL) under an argon atmosphere at −78° C. After the mixture was stirred at −78° C. for 10 minutes, a solution of methyl 4-formyl-3-hydroxybenzoate (0.18 g) in tetrahydrofuran (5 mL) was added to the reaction mixture. After the mixture was stirred under ice-cooling for 45 minutes, a saturated aqueous ammonium chloride solution and water were added to the reaction mixture, and the mixture was extracted with ethyl acetate. The extract was washed with water and dried over anhydrous magnesium sulfate, and the solvent was removed under reduced pressure. The residue was purified by column chromatography on silica gel (eluent: hexane/ethyl acetate=3/1) to give a diphenylmethanol compound (0.27 g). The obtained diphenylmethanol compound (0.27 g) was dissolved in methanol (5 mL), and concentrated hydrochloric acid (0.08 mL) and 10% palladium-carbon powder (54 mg) were added to the solution. After the mixture was stirred under a hydrogen atmosphere at room temperature for 18 hours, the catalyst was removed by filtration, and the filtrate was concentrated under reduced pressure. The residue was purified by column chromatography on silica gel (eluent: hexane/ethyl acetate=3/1) to give methyl 4-(4-ethylbenzyl)-3-hydroxybenzoate (0.20 g).
$^1$H-NMR (CDCl$_3$) δ ppm:
1.22 (3H, t, J=7.6 Hz), 2.62 (2H, q, J=7.6 Hz), 3.89 (3H, s), 4.00 (2H, s), 5.01 (1H, s), 7.05-7.25 (5H, m), 7.47 (1H, d, J=1.6 Hz), 7.56 (1H, dd, J=1.6, 7.8 Hz)

REFERENCE EXAMPLE 3

Methyl 3-hydroxy-4-(4-propoxybenzyl)benzoate

To a solution of 1-allyloxy-4-bromobenzene (3.1 g) in tetrahydrofuran (70 mL) was added 1.45 mol/L tert-butyllithium n-pentane solution (11 mL) under an argon atmosphere at −78° C. After the mixture was stirred at −78° C. for 5 minutes, a solution of methyl 4-formyl-3-hydroxybenzoate (0.89 g) in tetrahydrofuran (15 mL) was added to the reaction mixture. After the mixture was stirred for 30 minutes under ice-cooling, a saturated aqueous ammonium chloride solution and water were added to the reaction mixture, and the mixture was extracted with ethyl acetate. The extract was washed with water and dried over anhydrous magnesium sulfate, and the solvent was removed under reduced pressure. The residue was purified by column chromatography on silica gel (eluent: hexane/ethyl acetate=3/1) to give a diphenylmethanol compound (0.99 g). The obtained diphenylmethanol compound (0.99 g) was dissolved in methanol (10 mL), and 10% palladium-carbon powder (0.30 g) was added to the solution. After the mixture was stirred under a hydrogen atmosphere at room temperature for 24 hours, the catalyst was removed by filtration, and the filtrate was concentrated under reduced pressure. The residue was purified by column chromatography on silica gel (eluent: hexane/ethyl acetate=3/1) to give methyl 3-hydroxy-4-(4-propoxybenzyl)benzoate (0.50 g).
$^1$H-NMR (CDCl$_3$) δ ppm:
1.02 (3H, t, J=7.4 Hz), 1.70-1.85 (2H, m), 3.80-3.95 (5H, m), 3.97 (2H, s), 4.99 (1H, s), 6.75-6.90 (2H, m), 7.05-7.20 (3H, m), 7.47 (1H, d, J=1.5 Hz), 7.56 (1H, dd, J=1.5, 7.8 Hz)

REFERENCE EXAMPLE 4

Methyl 3-hydroxy-4-[4-(2-hydroxyethyl)benzyl]benzoate

To a solution of 2-(bromophenyl)ethylalcohol (1.7 g) in tetrahydrofuran (100 mL) was added 1.45 mol/L tert-butyllithium n-pentane solution (12.6 mL) under an argon atmosphere at −78° C. After the mixture was stirred at −78° C. for 10 minutes, a solution of methyl 4-formyl-3-hydroxybenzoate (0.50 g) in tetrahydrofuran (10 mL) was added to the reaction mixture. After the reaction mixture was stirred for 30 minutes under ice-cooling, a saturated aqueous ammonium chloride solution and water were added to the reaction mixture, and the mixture was extracted with ethyl acetate. The extract was washed with water and dried over anhydrous magnesium sulfate, and the solvent was removed under reduced pressure. The residue was purified by column chromatography on silica gel (eluent: hexane/ethyl acetate=1/3) to give a diphenylmethanol compound (0.28 g). The obtained diphenylmethanol compound (0.28 g) was dissolved in methanol (5 mL), and 10% palladium-carbon powder (0.14 g) was added to the solution. After the mixture was stirred at room temperature for 14 hours under a hydrogen atmosphere, the catalyst was removed by filtration, and the filtrate was concentrated under reduced pressure. The residue was purified by column chromatography on silica gel (eluent: hexane/ethyl acetate=1/1) to give methyl 3-hydroxy-4-[4-(2-hydroxyethyl)benzyl]benzoate (0.26 g).

$^1$H-NMR (CDCl$_3$) δ ppm:
1.37 (1H, t, J=5.9 Hz), 2.84 (2H, t, J=6.5 Hz), 3.75-3.95 (5H, m), 4.01 (2H, s), 5.10 (1H, s), 7.05-7.25 (5H, m), 7.47 (1H, d, J=1.6 Hz), 7.56 (1H, dd, J=1.6, 7.8 Hz)

REFERENCE EXAMPLE 5

2-(4-Isobutylbenzyl)phenol

A Grignard reagent was prepared from 2-benzyloxy-bromobenzene (0.20 g), magnesium (0.026 g), a catalytic amount of iodine and tetrahydrofuran (1 mL). The obtained Grignard reagent was added to a solution of 4-isobutylbenzaldehyde (0.16 g) in tetrahydrofuran (2 mL), and the mixture was stirred at room temperature for 30 minutes. The reaction mixture was purified by column chromatography on aminopropyl silica gel (eluent: tetrahydrofuran) to give a diphenylmethanol compound (0.23 g). The obtained diphenylmethanol compound was dissolved in ethanol (3 mL) and concentrated hydrochloric acid (0.1 mL). To the solution was added a catalytic amount of 10% palladium-carbon powder, and the mixture was stirred under a hydrogen atmosphere at room temperature overnight. The catalyst was removed by filtration, and the filtrate was concentrated under reduced pressure. The residue was purified by column chromatography on silica gel (eluent: dichloromethane/hexane=1/1) to give 2-(4-isobutylbenzyl)phenol (0.10 g).

$^1$H-NMR (CDCl$_3$) δ ppm:
0.89 (6H, d, J=6.6 Hz), 1.75-1.90 (1H, m), 2.43 (2H, d, J=7.2 Hz), 3.97 (2H, s), 4.66 (1H, s), 6.75-6.85 (1H, m), 6.85-6.95 (1H, m), 7.00-7.20 (6H, m)

REFERENCE EXAMPLE 6

2-(4-Isopropoxybenzyl)phenol

The title compound was prepared in a similar manner to that described in Reference Example 5 using 4-isopropoxybenzaldehyde instead of 4-isobutylbenzaldehyde.

$^1$H-NMR (CDCl$_3$) δ ppm:
1.31 (6H, d, J=6.1 Hz), 3.93 (2H, s), 4.50 (1H, heptet, J=6.1 Hz), 4.72 (1H, s), 6.75-6.85 (3H, m), 6.85-6.95 (1H, m), 7.05-7.20 (4H, m)

REFERENCE EXAMPLE 7

2-(4-Ethoxybenzyl)phenol

A Grignard reagent was prepared from 4-ethoxybromobenzene (1.5 g), magnesium (0.19 g), a catalytic amount of iodine and tetrahydrofuran (2 mL) in the usual manner. To the obtained Grignard reagent solution was added dropwise a solution of 2-benzyloxybenzaldehyde (1.1 g) in tetrahydrofuran (15 mL), and the mixture was stirred at room temperature for 30 minutes. To the reaction mixture were added a saturated aqueous ammonium chloride solution (10 mL) and water (20 mL), and the mixture was extracted with ethyl acetate (100 mL). The extract was washed with water (20 mL) and brine (20 mL), and dried over anhydrous sodium sulfate. Thereafter, the solvent was removed under reduced pressure. The residue was purified by column chromatography on silica gel (eluent: hexane/ethyl acetate=5/1) to give a diphenylmethanol compound (1.7 g). The obtained diphenylmethanol compound (1.7 g) was dissolved in ethanol (25 mL). To the solution were added concentrated hydrochloric acid (0.42 mL) and a catalytic amount of 10% palladium-carbon, and the mixture was stirred under a hydrogen atmosphere at room temperature for 18 hours. The catalyst was removed by filtration, and the filtrate was concentrated under reduced pressure. To the residue was added ethyl acetate (100 mL), and the mixture was washed with a saturated aqueous sodium hydrogen carbonate solution (30 mL) and brine (30 mL). The organic layer was dried over anhydrous sodium sulfate, and the solvent was removed under reduced pressure. The residue was purified by column chromatography on silica gel (eluent: hexane/ethyl acetate=8/1) to give 2-(4-ethoxybenzyl)phenol (0.85 g).

$^1$H-NMR (CDCl$_3$) δ ppm:
1.39 (3H, t, J=7.1 Hz), 3.93 (2H, s), 4.00 (2H, q, J=7.1 Hz), 4.72 (1H, s), 6.75-6.85 (3H, m), 6.85-6.95 (1H, m), 7.05-7.20 (4H, m)

REFERENCE EXAMPLE 8

2-[4-(3-Benzoyloxypropyl)benzyl]phenol

A Grignard reagent was prepared from 4-(3-benzyloxypropyl)bromobenzene (3.2 g), magnesium (0.25 g), a catalytic amount of iodine and tetrahydrofuran (10.5 mL). To the obtained Grignard reagent solution was added a solution of 2-(methoxymethoxy) benzaldehyde (1.1 g) in tetrahydrofuran (24 mL), and the mixture was stirred at 65° C. for 25 minutes. After cooling to ambient temperature, a saturated aqueous ammonium chloride solution (10 mL) and water (20 mL) were added to the reaction mixture, and the mixture was extracted with ethyl acetate (100 mL). The extract was washed with water (20 mL) and brine (20 mL). After the extract was dried over anhydrous sodium sulfate, the solvent was removed under reduced pressure, and the residue was purified by column chromatography on silica gel (eluent: hexane/ethyl acetate=5/1) to give a diphenylmethanol compound (2.5 g). The obtained diphenylmethanol compound (2.5 g) was dissolved in ethanol (42 mL), a catalytic amount of 10% palladium-carbon powder was added to the solution, and the mixture was stirred under a hydrogen atmosphere at room temperature for 7.5 hours. The catalyst was removed by filtration, and the filtrate was concentrated under reduced pressure. The residue was purified by column chromatography on silica gel (eluent: hexane/ethyl acetate=5/2) to give a phenylpropanol compound (1.6 g). After the obtained phenylpropanol compound (1.6 g) was dissolved in dichloromethane (29 mL), 4-(dimethylamino)pyridine (0.069 g), triethylamine (1.0 mL) and benzoyl chloride (0.79 mL) were added to the solution, and the mixture was stirred at room temperature for 3 hours. To the reaction mixture were added ethyl acetate (100 mL) and water (30 mL), and the organic layer was separated. The extract was washed with brine (30 mL) and dried over anhydrous sodium sulfate, and the solvent was removed under reduced pressure. The residue was purified by column chromatography on silica gel (eluent: hexane/ethyl acetate=20/1) to give an ester compound (2.2 g). A mixture of the obtained ester compound (2.2 g), p-toluenesulfonic acid monohydrate (0.21 g) and methanol (28 mL) was stirred at room temperature for 24 hours. The reaction mixture was concentrated under reduced pressure, and the residue was purified by column chromatography on silica gel (eluent: hexane/ethyl acetate=5/1) to give 2-[4-(3-benzoyloxypropyl)benzyl]phenol (1.8 g).

$^1$H-NMR (CDCl$_3$) δ ppm:
2.00-2.15 (2H, m), 2.70-2.80 (2H, m), 3.96 (2H, s), 4.33 (2H, t, J=6.5 Hz), 4.74 (1H, br s), 6.75-6.85 (1H, m), 6.85-

6.95 (1H, m), 7.05-7.20 (6H, m), 7.35-7.50 (2H, m), 7.50-7.65 (1H, m), 8.00-8.10 (2H, m)

REFERENCE EXAMPLE 9

2-[4-(2-Benzoyloxyethyl)benzyl]phenol

The title compound was prepared in a similar manner to that described in Reference Example 8 using 4-(2-benzyloxyethyl)bromobenzene instead of 4-(3-benzyloxypropyl)bromobenzene.

$^1$H-NMR (CDCl$_3$) δ ppm:
3.04 (2H, t, J=7.1 Hz), 3.98 (2H, s), 4.51 (2H, t, J=7.1 Hz), 4.66 (1H, s), 6.75-6.85 (1H, m), 6.85-6.95 (1H, m), 7.05-7.25 (6H, m), 7.35-7.50 (2H, m), 7.50-7.60 (1H, m), 7.95-8.05 (2H, m)

REFERENCE EXAMPLE 10

5-Acetoxymethyl-2-(4-ethylbenzyl)phenol

To a suspension of lithium aluminum hydride (95 mg) in diethyl ether (10 mL) was added a solution of methyl 4-(4-ethylbenzyl)-3-hydroxybenzoate (0.27 g) in diethyl ether (5 mL) under ice-cooling. After the mixture was heated under reflux for 45 minutes, water (0.1 mL), 15% aqueous sodium hydroxide solution (00.1 mL) and water (0.3 mL) were added successively to the reaction mixture under ice-cooling. After the mixture was stirred at room temperature for 5 minutes, the reaction mixture was poured into 0.5 mol/L hydrochloric acid, and the resulting mixture was extracted with ethyl acetate. The extract was dried over anhydrous magnesium sulfate, and the solvent was removed under reduced pressure. The residue was purified by column chromatography on silica gel (eluent: hexane/ethyl acetate=1/1) to give a reduced compound (0.22 g). After the obtained reduced compound (0.22 g) was dissolved in tetrahydrofuran (2 mL), vinyl acetate (2 mL) and bis(dibutylchlorotin)oxide (24 mg) were added to the solution, and the mixture was stirred at 30° C. for 19 hours. The reaction mixture was purified directly by column chromatography on silica gel (eluent: hexane/ethyl acetate=3/1) to give 5-acetoxymethyl-2-(4-ethylbenzyl)phenol (0.21 g).

$^1$H-NMR (CDCl$_3$) δ ppm:
1.21 (3H, t, J=7.6 Hz), 2.09 (3H, s), 2.61 (2H, q, J=7.6 Hz), 3.95 (2H, s), 4.74 (1H, s), 5.03 (2H, s), 6.80 (1H, d, J=1.3 Hz), 6.80-6.90 (1H, m), 7.05-7.20 (5H, m)

REFERENCE EXAMPLE 11

5-Acetoxymethyl-2-(4-propoxybenzyl)phenol

The title compound was prepared in a similar manner to that described in Reference Example 10 using methyl 3-hydroxy-4-(4-propoxybenzyl)benzoate instead of methyl 4-(4-ethylbenzyl)-3-hydroxybenzoate.

$^1$H-NMR (CDCl$_3$) δ ppm:
1.02 (3H, t, J=7.4 Hz), 1.70-1.85 (2H, m), 2.09 (3H, s), 3.88 (2H, t, J=6.6 Hz), 3.91 (2H, s), 5.02 (2H, s), 5.28 (1H, s), 6.70-6.90 (4H, m), 7.00-7.20 (3H, m)

REFERENCE EXAMPLE 12

2-[4-(2-Acetoxyethyl)benzyl]-5-acetoxymethylphenol

The title compound was prepared in a similar manner to that described in Reference Example 10 using methyl 3-hydroxy-4-[4-(2-hydroxyethyl)benzyl]benzoate instead of methyl 4-(4-ethylbenzyl)-3-hydroxybenzoate.

$^1$H-NMR (CDCl$_3$) δ ppm:
2.03 (3H, s), 2.09 (3H, s), 2.90 (2H, t, J=7.1 Hz), 3.96 (2H, s), 4.25 (2H, t, J=7.1 Hz), 4.82 (1H, s), 5.03 (2H, s), 6.80 (1H, d, J=1.5 Hz), 6.87 (1H, dd, J=1.5, 7.7 Hz), 7.05-7.20 (5H, m)

REFERENCE EXAMPLE 13

2-(4-Ethylthiobenzyl)phenol

A Grignard reagent was prepared from 1-bromo-4-(ethylthio)benzene (1.1 g), magnesium (0.12 g), a catalytic amount of iodine and tetrahydrofuran (5 mL). To the Grignard reagent solution was added a solution of 2-(methoxymethoxy)-benzaldehyde (0.56 g) in tetrahydrofuran (12 mL), and the mixture was stirred at 65° C. for 10 minutes. After cooling to ambient temperature, a saturated aqueous ammonium chloride solution (5 mL) and water (20 mL) were added to the reaction mixture, and the mixture was extracted with ethyl acetate (80 mL). The extract was washed with water (20 mL) and brine (20 mL), dried over anhydrous sodium sulfate, then the solvent was removed under reduced pressure. The residue was purified by column chromatography on silica gel (eluent: hexane/ethyl acetate=4/1) to give a diphenylmethanol compound (0.91 g). The obtained diphenylmethanol compound (0.90 g) was dissolved in dichloromethane (15 mL). To the solution was added a Dess-Martin reagent (1,1,1-tri(acetyloxy)-1,1-dihydro-1,2-benziodoxol-3(1H)-one) (1.5 g), and the mixture was stirred at 25° C. for 26 hours. To the reaction mixture were added diethyl ether (75 mL) and 1 mol/L aqueous sodium hydroxide solution (30 mL), the mixture was stirred vigorously, and the organic layer was separated. The organic layer was washed with 1 mol/L aqueous sodium hydroxide solution (30 mL), water (30 mL, 3 times) and brine (30 mL), dried over anhydrous sodium sulfate, and the solvent was removed under reduced pressure. The residue was purified by column chromatography on silica gel (eluent: hexane/ethyl acetate=15/1-9/1) to afford a ketone compound (0.82 g). A mixture of the obtained ketone compound (0.81 g), p-toluene-sulfonic acid monohydrate (0.10 g) and methanol (14 mL) was stirred at 60° C. for 4 hours. After cooling to ambient temperature, the reaction mixture was concentrated under reduced pressure. The residue was purified by column chromatography on silica gel (eluent: hexane/ethyl acetate=15/1) to give a deprotected compound (0.69 g). The obtained deprotected compound (0.68 g) was dissolved in tetrahydrofuran (11 mL), triethylamine (0.41 mL) and methyl chloroformate (0.22 mL) were added to the solution, and the mixture was stirred at 25° C. for 1 hour. Furthermore, triethylamine (0.11 mL) and methyl chloroformate (0.061 mL) were added to the reaction mixture, and the mixture was stirred for 30 minutes. The reaction mixture was filtered, and the filtrate was concentrated under reduced pressure. The residue was dissolved in tetrahydrofuran (14 mL) and water (7 mL), sodium borohydride (0.40 g) was added to the solution, and the mixture was stirred at 25° C. for 7 hours. To the reaction mixture was added dropwise 1 mol/L hydrochloric acid (15 mL), and the mixture was extracted with ethyl acetate (75 mL). The extract was washed with water (20 mL), a saturated aqueous sodium hydrogen carbonate solution (20 mL) and brine (20 mL), dried over anhydrous sodium sulfate, and the solvent was removed under reduced pressure. The residue was purified by column chromatography on silica gel (eluent: hexane/ethyl acetate=8/1) to give 2-(4-ethylthiobenzyl)phenol (0.62 g).

¹H-NMR (CDCl₃) δ ppm:
1.29 (3H, t, J=7.3 Hz), 2.90 (2H, q, J=7.3 Hz), 3.96 (2H, s), 4.62 (1H, s), 6.75-6.80 (1H, m), 6.85-6.95 (1H, m), 7.05-7.20 (4H, m), 7.20-7.30 (2H, m)

REFERENCE EXAMPLE 14

2-(4-Methoxybenzyl)phenyl 2,3,4,6-tetra-O-acetyl-β-D-glucopyranoside

To a solution of 2-(4-methoxybenzyl)phenol (46 mg) and 2,3,4,6-tetra-O-acetyl-1-O-trichloroacetoimidoyl-α-D-glucopyranose (0.13 g) in dichloromethane (2 mL) was added boron trifluoride diethyl ether complex (0.033 mL), and the mixture was stirred at room temperature for 1 hour. The reaction mixture was purified by column chromatography on aminopropyl silica gel (eluent: dichloromethane) to give 2-(4-methoxybenzyl)phenyl 2,3,4,6-tetra-O-acetyl-β-D-glucopyranoside (0.11 g).
¹H-NMR (CDCl₃) δ ppm:
1.91 (3H, s), 2.03 (3H, s), 2.05 (3H, s), 2.08 (3H, s), 3.77 (3H, s), 3.80-3.95 (3H, m), 4.17 (1H, dd, J=2.5, 12.2 Hz), 4.29 (1H, dd, J=5.5, 12.2 Hz), 5.11 (1H, d, J=7.5 Hz), 5.10-5.25 (1H, m), 5.25-5.40 (2H, m), 6.75-6.85 (2H, m), 6.95-7.10 (5H, m), 7.10-7.25 (1H, m)

REFERENCE EXAMPLE 15

2-(4-Methylbenzyl)phenyl 2,3,4,6-tetra-O-acetyl-β-D-glucopyranoside

The title compound was prepared in a similar manner to that described in Reference Example 14 using 2-(4-methylbenzyl)phenol instead of 2-(4-methoxybenzyl)phenol.
¹H-NMR (CDCl₃) δ ppm:
1.89 (3H, s), 2.03 (3H, s), 2.05 (3H, s), 2.07 (3H, s), 2.30 (3H, s), 3.80-3.95 (3H, m), 4.17 (1H, dd, J=2.5, 12.3 Hz), 4.28 (1H, dd, J=5.5, 12.3 Hz), 5.11 (1H, d, J=7.5 Hz), 5.10-5.25 (1H, m), 5.25-5.40 (2H, m), 6.90-7.20 (8H, m)

REFERENCE EXAMPLE 16

2-(4-Ethylbenzyl)phenyl 2,3,4,6-tetra-O-acetyl-β-D-glucopyranoside

The title compound was prepared in a similar manner to that described in Reference Example 14 using 2-(4-ethylbenzyl)phenol instead of 2-(4-methoxybenzyl)phenol.
¹H-NMR (CDCl₃) δ ppm:
1.20 (3H, t, J=7.6 Hz), 1.87 (3H, s), 2.03 (3H, s), 2.05 (3H, s), 2.08 (3H, s), 2.60 (2H, q, J=7.6 Hz), 3.80-4.00 (3H, m), 4.18 (1H, dd, J=2.3, 12.2 Hz), 4.28 (1H, dd, J=5.4, 12.2 Hz), 5.11 (1H, d, J=7.5 Hz), 5.10-5.25 (1H, m), 5.25-5.40 (2H, m), 6.90-7.25 (8H, m)

REFERENCE EXAMPLE 17

2-(4-Isobutylbenzyl)phenyl 2,3,4,6-tetra-O-acetyl-β-D-glucopyranoside

The title compound was prepared in a similar manner to that described in Reference Example 14 using 2-(4-isobutylbenzyl)phenol instead of 2-(4-methoxybenzyl)phenol.
¹H-NMR (CDCl₃) δ ppm:
0.88 (6H, d, J=6.6 Hz), 1.75-1.90 (1H, m), 1.87 (3H, s), 2.03 (3H, s), 2.05 (3H, s), 2.08 (3H, s), 2.42 (2H, d, J=7.2 Hz), 3.80-3.95 (3H, m), 4.18 (1H, dd, J=2.4, 12.3 Hz), 4.29 (1H, dd, J=5.5, 12.3 Hz), 5.11 (1H, d, J=7.6 Hz), 5.10-5.25 (1H, m), 5.25-5.40 (2H, m), 6.90-7.25 (8H, m)

REFERENCE EXAMPLE 18

2-(4-Ethoxybenzyl)phenyl 2,3,4,6-tetra-O-acetyl-β-D-glucopyranoside

The title compound was prepared in a similar manner to that described in Reference Example 14 using 2-(4-ethoxybenzyl)phenol instead of 2-(4-methoxybenzyl)phenol.
¹H-NMR (CDCl₃) δ ppm:
1.39 (3H, t, J=7.0 Hz), 1.91 (3H, s), 2.03 (3H, s), 2.05 (3H, s), 2.07 (3H, s), 3.80-3.95 (3H, m), 3.99 (2H, q, J=7.0 Hz), 4.18 (1H, dd, J=2.5, 12.3 Hz), 4.28 (1H, dd, J=5.6, 12.3 Hz), 5.10 (1H, d, J=7.7 Hz), 5.15-5.25 (1H, m), 5.25-5.40 (2H, m), 6.75-6.85 (2H, m), 6.95-7.10 (5H, m), 7.10-7.20 (1H, m)

REFERENCE EXAMPLE 19

2-(4-Isopropoxybenzyl)phenyl 2,3,4,6-tetra-O-acetyl-β-D-glucopyranoside

The title compound was prepared in a similar manner to that described in Reference Example 14 using 2-(4-isopropoxy-benzyl)phenol instead of 2-(4-methoxybenzyl)phenol.
¹H-NMR (CDCl₃) δ ppm:
1.30 (6H, d, J=6.0 Hz), 1.90 (3H, s), 2.03 (3H, s), 2.05 (3H, s), 2.08 (3H, s), 3.80-3.90 (3H, m), 4.18 (1H, dd, J=2.3, 12.3 Hz), 4.28 (1H, dd, J=5.5, 12.3 Hz), 4.48 (1H, heptet, J=6.0 Hz), 5.10 (1H, d, J=7.7 Hz), 5.10-5.25 (1H, m), 5.25-5.40 (2H, m), 6.70-6.85 (2H, m), 6.90-7.10 (5H, m), 7.10-7.20 (1H, m)

REFERENCE EXAMPLE 20

5-Acetoxymethyl-2-(4-ethylbenzyl)phenyl 2,3,4,6-tetra-O-acetyl-β-D-glucopyranoside The title compound was prepared in a similar manner to that described in Reference Example 14 using 5-acetoxymethyl-2-(4-ethylbenzyl)phenol instead of 2-(4-methoxybenzyl)phenol.
¹H-NMR (CDCl₃) δ ppm:
1.20 (3H, t, J=7.6 Hz), 1.88 (3H, s), 2.02 (3H, s), 2.05 (3H, s), 2.07 (3H, s), 2.09 (3H, s), 2.60 (2H, q, J=7.6 Hz), 3.80-3.95 (3H, m), 4.20 (1H, dd, J=2.4, 12.3 Hz), 4.27 (1H, dd, J=5.3, 12.3 Hz), 5.00-5.10 (2H, m), 5.13 (1H, d, J=7.4 Hz), 5.15-5.40 (3H, m), 6.95-7.15 (7H, m)

REFERENCE EXAMPLE 21

Acetoxymethyl-2-(4-propoxybenzyl)phenyl 2,3,4,6-tetra-O-acetyl-β-D-glucopyranoside The title compound was prepared in a similar manner to that described in Reference Example 14 using 5-acetoxymethyl-2-(4-propoxybenzyl)phenol instead of 2-(4-methoxybenzyl)phenol.
¹H-NMR (CDCl₃) δ ppm:
1.01 (3H, t, J=7.4 Hz), 1.70-1.85 (2H, m), 1.92 (3H, s), 2.03 (3H, s), 2.05 (3H, s), 2.07 (3H, s), 2.09 (3H, s), 3.80-3.95 (5H, m), 4.20 (1H, dd, J=2.4, 12.3 Hz), 4.27 (1H, dd, J=5.3, 12.3 Hz), 5.00-5.10 (2H, m), 5.12 (1H, d, J=7.4 Hz), 5.15-5.40 (3H, m), 6.75-6.85 (2H, m), 6.95-7.10 (5H, m)

REFERENCE EXAMPLE 22

2-[4-(2-Acetoxyethyl)benzyl]-5-acetoxymethylphenyl 2,3,4,6-tetra-O-acetyl-β-D-glucopyranoside The title compound was prepared in a similar manner to that described in Reference Example 14 using 2-[4-(2-acetoxyethyl)benzyl]-5-acetoxymethylphenol instead of 2-(4-methoxybenzyl)phenol.

$^1$H-NMR (CDCl$_3$) δ ppm:
1.89 (3H, s), 2.03 (3H, s), 2.03 (3H, s), 2.05 (3H, s), 2.07 (3H, s), 2.09 (3H, s), 2.88 (2H, t, J=7.1 Hz), 3.85-3.95 (3H, m), 4.15-4.35 (4H, m), 5.00-5.10 (2H, m), 5.13 (1H, d, J=7.5 Hz), 5.15-5.40 (3H, m), 6.95-7.15 (7H, m)

EXAMPLE 1

2-(4-Methoxybenzyl)phenyl β-D-glucopyranoside

Sodium methoxide (28% methanol solution; 0.12 mL) was added to a solution of 2-(4-methoxybenzyl)phenyl 2,3,4,6-tetra-O-acetyl-β-D-glucopyranoside (0.11 g) in methanol (4 mL) and the mixture was stirred at room temperature for 30 minutes. The solvent was removed under reduced pressure. The residue was purified by column chromatography on silica gel (eluent: dichloromethane/methanol=10/1) to give 2-(4-methoxybenzyl)phenyl β-D-glucopyranoside (65 mg).

$^1$H-NMR (CD$_3$OD) δ ppm:
3.35-3.55 (4H, m), 3.69 (1H, dd, J=5.1, 12.1 Hz), 3.73 (3H, s), 3.80-4.00 (2H, m), 4.03 (1H, d, J=15.1 Hz), 4.91 (1H, d, J=7.4 Hz), 6.75-6.85 (2H, m), 6.85-6.95 (1H, m), 6.95-7.10 (1H, m), 7.10-7.20 (4H, m)

EXAMPLE 2

2-(4-Methylbenzyl)phenyl β-D-glucopyranoside

The title compound was prepared in a similar manner to that described in Example 1 using 2-(4-methylbenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
2.27 (3H, s), 3.35-3.55 (4H, m), 3.69 (1H, dd, J=5.2, 12.0 Hz), 3.80-3.90 (1H, m), 3.94 (1H, d, J=15.0 Hz), 4.05 (1H, d, J=15.0 Hz), 4.85-4.95 (1H, m), 6.85-6.95 (1H, m), 6.95-7.20 (7H, m)

EXAMPLE 3

2-(4-Ethylbenzyl)phenyl β-D-glucopyranoside

The title compound was prepared in a similar manner to that described in Example 1 using 2-(4-ethylbenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
1.15-1.25 (3H, m), 2.50-2.65 (2H, m), 3.35-3.55 (4H, m), 3.65-3.75 (1H, m), 3.80-4.00 (2H, m), 4.06 (1H, d, J=14.9 Hz), 4.85-5.00 (1H, m), 6.85-7.00 (1H, m), 7.00-7.20 (7H, m)

EXAMPLE 4

2-(4-Isobutylbenzyl)phenyl β-D-glucopyranoside

The title compound was prepared in a similar manner to that described in Example 1 using 2-(4-isobutylbenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
0.80-0.95 (6H, m), 1.70-1.90 (1H, m), 2.41 (2H, d, J=7.1 Hz), 3.30-3.55 (4H, m), 3.60-3.75 (1H, m), 3.80-3.95 (1H, m), 3.95 (1H, d, J=15.0 Hz), 4.06 (1H, d, J=15.0 Hz), 4.85-4.95 (1H, m), 6.80-7.20 (8H, m)

EXAMPLE 5

2-(4-Ethoxybenzyl)phenyl β-D-glucopyranoside

The title compound was prepared in a similar manner to that described in Example 1 using 2-(4-ethoxybenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
1.35 (3H, t, J=6.8 Hz), 3.35-3.55 (4H, m), 3.60-3.75 (1H, m), 3.80-4.10 (5H, m), 4.90 (1H, d, J=7.1 Hz), 6.70-6.85 (2H, m), 6.85-6.95 (1H, m), 7.00-7.20 (5H, m)

EXAMPLE 6

2-(4-Isopropoxybenzyl)phenyl β-D-Glucopyranoside

The title compound was prepared in a similar manner to that described in Example 1 using 2-(4-isopropoxybenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
1.27 (6H, d, J=6.0 Hz), 3.35-3.55 (4H, m), 3.69 (1H, dd, J=5.4, 12.1 Hz), 3.88 (1H, dd, J=2.0, 12.1 Hz), 3.91 (1H, d, J=15.0 Hz), 4.02 (1H, d, J=15.0 Hz), 4.51 (1H, heptet, J=6.0 Hz), 4.91 (1H, d, J=7.7 Hz), 6.70-6.85 (2H, m), 6.85-6.95 (1H, m), 7.00-7.10 (1H, m), 7.10-7.20 (4H, m)

Example 7

5-Hydroxymethyl-2-(4-propoxybenzyl)phenyl β-D-glucopyranoside

The title compound was prepared in a similar manner to that described in Example 1 using 5-acetoxymethyl-2-(4-propoxybenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
1.02 (3H, t, J=7.4 Hz), 1.70-1.85 (2H, m), 3.30-3.55 (4H, m), 3.65-3.75 (1H, m), 3.80-3.95 (4H, m), 4.00 (1H, d, J=15.0 Hz), 4.54 (2H, s), 4.93 (1H, d, J=7.4 Hz), 6.70-6.85 (2H, m), 6.85-6.95 (1H, m), 7.02 (1H, d, J=7.7 Hz), 7.05-7.20 (3H, m)

EXAMPLE 8

2-(4-Ethylbenzyl)-5-hydroxymethylphenyl β-D-glucopyranoside

The title compound was prepared in a similar manner to that described in Example 1 using 5-acetoxymethyl-2-(4-ethylbenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:
1.19 (3H, t, J=7.6 Hz), 2.57 (2H, q, J=7.6 Hz), 3.30-3.55 (4H, m), 3.65-3.75 (1H, m), 3.85-4.00 (2H, m), 4.04 (1H, d, J=15.0 Hz), 4.54 (2H, s), 4.93 (1H, d, J=7.4 Hz), 6.85-6.95 (1H, m), 7.02 (1H, d, J=7.7 Hz), 7.06 (2H, d, J=8.1 Hz), 7.10-7.20 (3H, m)

EXAMPLE 9

2-[4-(2-Hydroxyethyl)benzyl]-5-hydroxymethylphenyl β-D-glucopyranoside

The title compound was prepared in a similar manner to that described in Example 1 using 2-[4-(2-acetoxyethyl)benzyl]-5-acetoxymethylphenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm:

2.76 (2H, t, J=7.1 Hz), 3.30-3.55 (4H, m), 3.60-3.75 (3H, m), 3.85-4.00 (2H, m), 4.05 (1H, d, J=14.6 Hz), 4.54 (2H, s), 4.92 (1H, d, J=7.2 Hz), 6.85-6.95 (1H, m), 7.03 (1H, d, J=7.9 Hz), 7.09 (2H, d, J=7.8 Hz), 7.10-7.20 (3H, m)

EXAMPLE 10

2-[4-(2-Hydroxyethyl)benzyl]phenyl β-D-glucopyranoside

To a solution of 2-[4-(2-benzoyloxyethyl)benzyl]phenol (0.49 g) and 1,2,3,4,6-penta-O-acetyl-β-D-glucopyranose (1.7 g) in toluene (5.2 mL) and dichloromethane (2.2 mL) was added boron trifluoride diethyl ether complex (0.56 mL), and the mixture was stirred at 25° C. for 8 hours. To the reaction mixture were added ethyl acetate (70 mL) and a saturated aqueous sodium hydrogen carbonate solution (25 mL), and the organic layer was separated. The organic layer was washed with brine (25 mL) and dried over anhydrous sodium sulfate, and the solvent was removed under reduced pressure. The residue was dissolved in methanol (5 mL) and tetrahydrofuran (2.5 mL), sodium methoxide (28% methanol solution, 0.14 mL) was added to the solution, and the resulting mixture was stirred at 25° C. for 12.5 hours. To the reaction mixture were added ethyl acetate (75 mL) and water (20 mL), and the organic layer was separated. The organic layer as washed with brine (20 mL) and dried over anhydrous sodium sulfate, and the solvent was removed under reduced pressure. The residue was dissolved in methanol (7.5 mL), sodium methoxide (28% methanol solution, 0.085 mL) was added to the solution, and the resulting mixture was stirred at 25° C. for 5 hours. The reaction mixture was purified by column chromatography on silica gel (eluent: dichloromethane/methanol=4/1). The solvent was removed under reduced pressure, diethyl ether was added to the residue, and the resulting precipitates were collected by filtration. The obtained solid was washed with diethyl ether and dried under reduced pressure to give 2-[4-(2-hydroxyethyl)benzyl]phenyl β-D-glucopyranoside (0.47 g).

$^1$H-NMR (CD$_3$OD) δ ppm:

2.76 (2H, t, J=7.1 Hz), 3.35-3.55 (4H, m), 3.65-3.75 (3H, m), 3.88 (1H, dd, J=1.8, 11.8 Hz), 3.95 (1H, d, J=15.2 Hz), 4.07 (1H, d, J=15.2 Hz), 4.90 (1H, d, J=7.4 Hz), 6.85-6.95 (1H, m), 7.00-7.20 (7H, m)

EXAMPLE 11

2-[4-(3-Hydroxypropyl)benzyl]phenyl β-D-glucopyranoside

The title compound was prepared in a similar manner to that described in Example 10 using 2-[4-(3-benzoyloxypropyl)benzyl]phenol instead of 2-[4-(2-benzoyloxyethyl)benzyl]phenol.

$^1$H-NMR (CD$_3$OD) δ ppm:

1.70-1.85 (2H, m), 2.55-2.65 (2H, m), 3.30-3.60 (6H, m), 3.69 (1H, dd, j=5.2, 11.9 Hz), 3.88 (1H, dd, J=2.0, 11.9 Hz), 3.95 (1H, d, J=15.1 Hz), 4.06 (1H, d, J=15.1 Hz), 4.90 (1H, d, J=7.3 Hz), 6.85-6.95 (1H, m), 7.00-7.20 (7H, m)

EXAMPLE 12

2-(4-Ethylthiobenzyl)phenyl β-D-glucopyranoside

To a solution of 2-(4-ethylthiobenzyl)phenol (0.51 g) and 1,2,3,4,6-penta-O-acetyl-β-D-glucopyranose (2.4 g) in toluene (6.3 mL) and dichloromethane (2.7 mL) was added boron trifluoride diethyl ether complex (0.78 mL), and the mixture was stirred at room temperature for 9 hours. To the reaction mixture were added ethyl acetate (70 mL) and a saturated aqueous sodium hydrogen carbonate solution (25 mL), and the organic layer was separated. The organic layer was washed with brine (25 mL), dried over anhydrous sodium sulfate, and the solvent was removed under reduced pressure. The residue was dissolved in methanol (10.5 mL), sodium methoxide (28% methanol solution, 0.08 mL) was added to the solution, and the mixture was stirred at 25° C. for 18 hours. To the reaction mixture were added ethyl acetate (75 mL) and water (20 mL), and the organic layer was separated. The organic layer was washed with brine (20 mL), dried over anhydrous sodium sulfate, and the solvent was removed under reduced pressure. The residue was purified by column chromatography on silica gel (eluent: dichloromethane/methanol=10/1). The solvent was removed under reduced pressure, diethyl ether was added to the residue, and the resulting precipitates were collected by filtration. The obtained colorless solid was washed with diethyl ether and dried under reduced pressure to give 2-(4-ethylthiobenzyl) phenyl β-D-glucopyranoside (0.51 g).

$^1$H-NMR (CD$_3$OD) δ ppm:

1.24 (3H, t, J=7.3 Hz), 2.88 (2H, q, J=7.3 Hz), 3.35-3.55 (4H, m), 3.69 (1H, dd, J=5.0, 12.2 Hz), 3.88 (1H, dd, J=2.0, 12.2 Hz), 3.95 (1H, d, J=15.1 Hz), 4.08 (1H, d, J=15.1 Hz), 4.91 (1H, d, J=7.3 Hz), 6.85-7.00 (1H, m), 7.00-7.10 (1H, m), 7.10-7.30 (6H, m)

TEST EXAMPLE 1

Assay for Inhibitory Effect on Human SGLT2 Activity 1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco- BRL: LIFE TECHNOLOGIES). DNA fragment coding for human SGLT2 was amplified by the Pfu DNA Polymerase (Stratagene)—used PCR reaction, in which the human kidney cDNA library described above was used as the template and the following oligo nucleotides 0702F and 0712R, presented as SEQ ID NO: 1 and SEQ ID NO:2 respectively, were used as the primers. The amplified DNA fragment was ligated into pCR-Blunt (Invitrogen), a vector for cloning, according to standard method of the kit. The competent cell, *Escherichia coli* HB101 (Toyobo), was transformed according to usual method and then selection of the transformants was performed on the LB agar medium containing 50 µtg/mL of kanamycin. After plasmid DNA was extracted and purified from the one of the transformants, amplifying of the DNA fragment coding for human SGLT2 was performed by the Pfu DNA Polymerase (Stratagene)—used PCR reaction, in which the following oligo nucleotides 0714F and 0715R, presented as SEQ ID NO: 3 and SEQ ID NO: 4 respectively, were used as the primers. The amplified DNA fragment was digested with restriction enzymes, Xho I and Hind III, and then purified with Wizard Purification System (Promega). This purified DNA fragment was inserted at the corresponding restriction enzyme sites of pcDNA3.1 (−) Myc/His-A (Invitrogen), a vector for expressing of fusion protein. The competent cell, *Escherichia coli* HE101 (Toyobo), was transformed according to usual method and then selection of the transformant was performed on the LB agar medium containing 100 µg/mL of ampicillin. After the plasmid DNA was extracted and purified from this transformant, the sequence of the DNA fragment inserted at the multi-cloning sites of the vector, pcDNA3.1 (−) Myc/His-A, was analyzed. This clone had a single base substitution (ATC which codes for the isoleucine-433 was substituted by GTC) compared with the human SGLT2 reported by Wells et al (Am. J. Physiol., Vol. 263, pp. 459-465 (1992)). Sequentially, a clone in which valine is substituted for isoleucine-433 was obtained. This plasmid vector expressing human SGLT2 in which the peptide presented as SEQ ID NO: 5 is fused to the carboxyl terminal alanine residue was designated KL29.

```
SEQ ID NO: 1    ATGGAGGAGCACACAGAGGC

SEQ ID NO: 2    GGCATAGAAGCCCCAGAGGA

SEQ ID NO: 3    AACCTCGAGATGGAGGAGCACACAGAGGC

SEQ ID NO: 4    AACAAGCTTGGCATAGAAGCCCCAGAGGA

SEQ ID NO: 5    KLGPEQKLISEEDLNSAVDHHHHHH
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 µF, $2 \times 10^6$ cells of COS-7 cell and 20 µg of KL29 in 500 µL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 µL of this cell suspension was added. After overnight culture at 37° C. under 5% $CO_2$, 125 µL of DMEM medium (Gibco-BRL: LIFE TECHNOLOGIES) which is containing 10% of fetal bovine serum (Sanko Jyunyaku), 100 units/mL sodium penicillin G (Gibco-BRL: LIFE TECHNOLOGIES), 100 µg/mL streptomycin sulfate (Gibco-BRL: LIFE TECHNOLOGIES) was added to each well. After a culture until the following day, these cells were used for measurement of the inhibitory activity against the uptake of methyl-α-D-glucopyranoside.

3) Measurement of the Inhibitory Activity Against the Uptake of methyl-α-D-glucopyranoside After removal of the medium of the COS-7 cells expressing transiently human SGLT2, to each well 200 µL of the pre-treatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)aminomethane) was added and the cells were incubated 37° C. for 10 minutes. The pretreatment buffer was removed and 200 µL of the same buffer was added again, and then the cells were incubated 37° C. for 10 minutes. Seven µL of methyl-α-D-(U-14C)glucopyranoside (Amersham Pharmacia Biotech) was added to 525 µL of the buffer for uptake containing test sample (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris(hydroxymethyl)aminomethane), and this mixture was mixed, and then the buffer for measurement of uptake was prepared. For the control, the buffer for measurement of uptake without test compound was prepared. For estimate of the basal uptake in the absence of test compound and sodium, the buffer for measurement of the basal uptake, which contains 140 mM choline chloride in place of sodium chloride, was prepared similarly. After the pretreatment buffer was removed, 75 µL of the buffer for measurement of uptake was added to each well, the cells were incubated at 37° C. for 2 hours. After the buffer for measurement of uptake was removed, 200 µL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris(hydroxymethyl)aminomethane) was added to each well and immediately removed. After two additional washing, the cells were solubilized by addition of 75 µL of 0.2 N sodium hydroxide to each well. After the cell lysates were transferred to the PicoPlate (Packard) and 150 µL of MicroScint-40 (Packard) was added to each well, the radioactivity was measured with microplate scintillation counter Top-Count (Packard). The difference in uptake was obtained as 100% value by subtracting the radioactivity in the basal uptake from that in control and then the concentrations at which 50% of uptake were inhibited ($IC_{50}$ value) were calculated from the concentration-inhibition curve by least square method. The results are shown in the following Table 1.

TABLE 1

| Test compound | IC$_{50}$ value (nM) |
|---|---|
| Example 1 | 350 |
| Example 2 | 450 |
| Example 3 | 140 |
| Example 4 | 500 |
| Example 5 | 330 |
| Example 6 | 370 |
| Example 7 | 140 |
| Example 8 | 8.1 |
| Example 9 | 27 |
| Example 10 | 210 |
| Example 11 | 75 |
| Example 12 | 110 |

TEST EXAMPLE 2

Assay for the Facilitatory Effect on Urinary Glucose Excretion

As experimental animal, overnight fasted SD rats (SLC., male, 7 weeks of age, 180-240 g) were used. Ten mg of test compound was suspended or dissolved in 300 μL of ethanol and then dissolved by adding of 1.2 mL of polyethylene glycol 400 and 1.5 mL of saline, and then 3.3 mg/mL solution was prepared. Three hundred μL of this solution was dissolved with 2.7 mL of the solution for dilution (saline: polyethylene glycol 400:ethanol=5:4:1) and then 0.33 mg/mL solution was prepared. After the body weights of rats were measured, the solution of test compound was intravenously injected to the tail vein at the dose of 3 mL/kg (1 mg/kg). For control, just only the solution (saline: polyethylene glycol 400:ethanol=5:4:1) was intravenously injected to the tail vein at the dose of 3 mL/kg. Immediately after intravenous injection to the tail vein, 200 g/L of glucose solution was orally administered to the rats at the dose of 10 mL/kg (2 g/kg). The intravenous injection to the tail vein was performed with 26 G injection needle and 1 mL syringe. The oral administration was performed with gastric tube for rat and 2.5 mL syringe. The head count in one group was 2 or 3. Collection of urine was performed in metabolic cage after the oral administration of glucose was finished. The sampling time for collection of urine was 24 hours after the oral administration of glucose. After the collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion in 24 hours per 200 g of body weight was calculated from urine volume, urinary glucose concentration and body weight. The results are shown in the following Table 2.

TABLE 2

| Test compound | Amount of urinary glucose excretion (mg) |
|---|---|
| Example 1 | 27.4 |
| Example 7 | 109.1 |
| Example 8 | 238.9 |
| Example 10 | 69.5 |

TEST EXAMPLE 3

Acute Toxicity Test

Five weeks old male ICR mice (CLEA JAPAN, INC. 29-34 g, 5 animals in each group) were fasted for 4 hours, and 666 mg/mL of a suspension which was prepared by adding saline: polyethylene glycol 400:ethanol (5:4:1) to 2-[4-(2-hydroxyethyl)benzyl]phenyl β-D-glucopyranoside (the compound described in Example 10) was subcutaneously administered at the dose of 3 mL/kg (2000 mg/kg). No death was observed until 24 hours after the administration.

INDUSTRIAL APPLICABILITY

The glucopyranosyloxybenzylbenzene derivatives represented by the above general formula (I) of the present invention have an excellent inhibitory activity in human SGLT2. The present invention can provide agents for the prevention or treatment of diabetes, diabetic complications, obesity or the like. In addition, since compounds represented by the above general formula (II) are important as intermediates in the production of the compounds represented by the above general formula (I), the compounds represented by the above general formula (I) of the present invention can be readily prepared via such compounds.

What is claimed is:

1. A method for the treatment of a disease associated with hyperglycemia, which comprises administering a glycopyranosyloxybenzylbenzene derivative represented by the general formula:

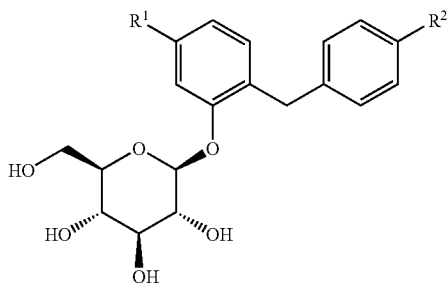

wherein $R^1$ represents a hydrogen atom or a hydroxy (lower alkyl) group; and $R^2$ represents a lower alkyl group, a lower alkoxy group, a lower alkylthio group, a hydroxy (lower alkyl) group, a hydroxy (lower alkoxy) group, a hydroxy (lower alkylthio) group, a lower alkoxy-substituted (lower alkyl) group, a lower alkoxy-substituted (lower alkoxy) group or a lower alkoxy-substituted (lower alkylthio) group, or a pharmaceutically acceptable salt thereof, to a patient in need of treatment of a disease associated with hyperglycemia.

2. The method for treatment as claimed in claim 1 wherein the disease associated with hyperglycemia is diabetes.

3. The method for treatment as claimed in claim 1 wherein the disease associated with hyperglycemia is obesity.

4. A method for the treatment of a disease associated with hyperglycemia, which comprises administering a glycopyranosyloxybenzylbenzene derivative represented by the general formula

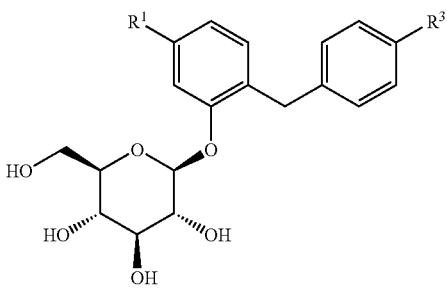

wherein $R^1$ represents a hydrogen atom or a hydroxy (lower alkyl) group; and $R^3$ represents a lower alkyl group, a lower alkoxy group, or a hydroxy (lower alkyl) group, or a pharmaceutically acceptable salt thereof, to a patient in need of treatment of a disease associated with hyperglycemia.

5. A method for treating diabetes, hyperglycemia, or obesity, which comprises administering to a mammalian species in need of treatment a therapeutically effective amount of a compound having the structure

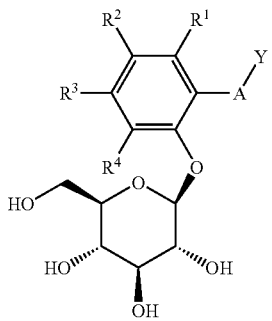

wherein:

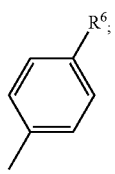

Y is $R^1$, $R^2$, $R^3$, and $R^4$ are hydrogen;

$R^6$ is selected form $OR^{7a}$, lower alkyl, $CHOHR^{8g}$, $CH(OR^{7h})R^{8h}$, and $-SR^{7e}$;

$R^{7a}$, $R^{7e}$, and $R^{7h}$ are lower alkyl;

$R^{8g}$ and $R^{8h}$ are alkyl; and

A is $(CH_2)_n$ where n is 1, or a pharmaceutically acceptable salt or stereoisomer thereof.

6. The method as defined in claim 5 where the compound administered has the structure:

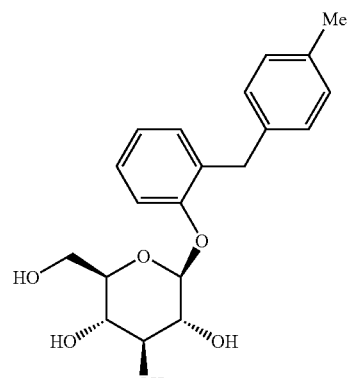

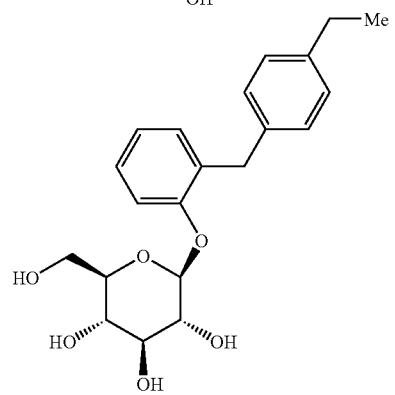

or

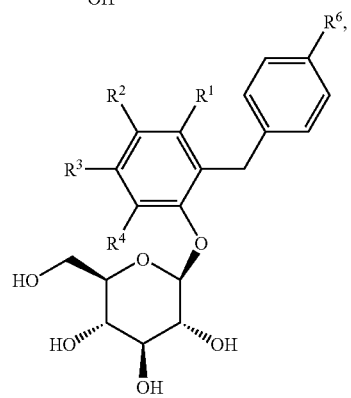

wherein $R^1$, $R^2$, $R^3$ and $R^4$ are H and $R^6$ is MeO.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: PCR primer 0702F

<400> SEQUENCE: 1
atggaggagc acacagaggc                                            20

<210> SEQ ID NO 2
<211> LENGTH: 20
<212> TYPE: DNA
<213> ORGANISM: Artificial Sequence

```
<220> FEATURE:
<223> OTHER INFORMATION: PCR primer 0712R

<400> SEQUENCE: 2
ggcatagaag ccccagagga                                            20

<210> SEQ ID NO 3
<211> LENGTH: 29
<212> TYPE: DNA
<213> ORGANISM: Artificial Sequence
<220> FEATURE:
<223> OTHER INFORMATION: PCR primer 0714F

<400> SEQUENCE: 3
aacctcgaga tggaggagca cacagaggc                                  29

<210> SEQ ID NO 4
<211> LENGTH: 29
<212> TYPE: DNA
<213> ORGANISM: Artificial Sequence
<220> FEATURE:
<223> OTHER INFORMATION: PCR primer 0715R

<400> SEQUENCE: 4
aacaagcttg gcatagaagc cccagagga                                  29

<210> SEQ ID NO 5
<211> LENGTH: 25
<212> TYPE: PRT
<213> ORGANISM: Artificial Sequence
<220> FEATURE:
<223> OTHER INFORMATION: SGLT2 carboxy-terminal sequence

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25
```